United States Patent [19]

Muszak

[11] Patent Number: 4,876,926
[45] Date of Patent: Oct. 31, 1989

[54] STOPPER REMOVER APPARATUS
[75] Inventor: Martin F. Muszak, Rochester, N.Y.
[73] Assignee: Eastman Kodak Company, Rochester, N.Y.
[21] Appl. No.: 310,159
[22] Filed: Feb. 14, 1989
[51] Int. Cl.[4] .................................................. B67B 7/02
[52] U.S. Cl. ......................................... 81/3.2; 81/3.31; 81/3.33
[58] Field of Search .......................... 81/3.07, 3.2, 3.25, 81/3.31, 3.33, 3.4

[56] References Cited

U.S. PATENT DOCUMENTS

| D. 193,899 | 10/1962 | Harrison ................................. | 81/3.4 |
| 1,593,947 | 7/1926 | Miller et al. ........................... | 81/3.4 |
| 1,924,579 | 8/1933 | Waterhouse . | |
| 2,023,975 | 12/1935 | Qualey . | |
| 2,631,482 | 3/1953 | Rinehart . | |
| 4,217,798 | 8/1980 | McCarthy et al. . | |

FOREIGN PATENT DOCUMENTS

| 264456 | 4/1988 | European Pat. Off. . |
| 3215647 | 4/1982 | Fed. Rep. of Germany . |
| 3141780 | 5/1983 | Fed. Rep. of Germany . |
| 2581980 | 11/1986 | France .................................. 81/3.36 |
| 62-6171 | 1/1987 | Japan . |

Primary Examiner—Roscoe V. Parker
Attorney, Agent, or Firm—Dana M. Schmidt

[57] ABSTRACT

There is described a stopper remover for automatically removing a stopper in a container, the remover comprising first mechanism for gripping the container against rotation, second mechanism for gripping the stopper, and a drive for rotating the second mechanism about an axis while the second mechanism grips a stopper. The remover features an engaging assembly for frictionally engaging a stopper while the rotating drive rotates in only one direction, the engaging assembly comprising an annular ring and extending from the inside of the ring, a plurality of spikes terminating in points disposed generally in an annular surface inside of the ring and constructed to engage a stopper, the spikes being mounted on the ring so as to be non-radially aligned. The result is that the spikes positively grip the stopper only if the ring is rotated in the one direction, and slip off the stopper when the rotating drive rotates in a direction opposite to the one direction.

4 Claims, 3 Drawing Sheets

STOPPER REMOVER APPARATUS

FIELD OF THE INVENTION

This invention relates to apparatus for automatically removing stoppers from containers of liquid, particularly those useful in analyzers.

BACKGROUND OF THE INVENTION

Automated means have been attempted for years to remove stoppers from test tubes or containers. Early approaches have been to "flip" out the stopper by leveraging one edge, as shown for example in U.S. Pat. No. 4,217,798 and German AUS No. 3,141,780. Such an approach creates the hazard of loose stoppers, or necessitates the use of a connector to secure unstoppered stoppers to their associated containers. To deal with this, more positive gripping means have been provided, for example devices using spikes that pierce the top of the stopper before pulling out the stopper, as shown in EPO No. 264,456. However, such piercing devices severly penetrate the stopper, and are not likely to be useful on stoppers or plugs made from relatively tough materials, e.g., plastic materials. Furthermore, the severe penetration of the stopper means that only a forceful withdrawal of the spikes will remove them from engagement with the stopper, as is necessary when restoppering the container. Such a forceful withdrawal requires pusher means of some kind, so that a simple reversal of part positions, e.g., the pulling apart of jaws on which the spikes are mounted, is apt to still leave the stopper impaled on one or more of the spikes.

Thus, there has been a need prior to this invention for an automatic stopper remover that positively engages the stopper to be removed, to keep from having loose stoppers, while at the same time provide for ready withdrawal of engagement of the stopper such as by reversing the action of the stopper gripping means.

SUMMARY OF THE INVENTION

I have developed an automated stopper remover apparatus that solves the aforementioned problems.

In accordance with the invention, there is provided a stopper remover for automatically removing a stopper in a open end of an otherwise closed liquid container, the remover comprising first means for gripping the container against rotation, second means for gripping the stopper, and means for rotating the second means about an axis while the second means grips a stopper. The remover is improved in that the second gripping means includes engaging means for frictionally engaging a stopper while the rotating means rotates in only one direction, the engaging means comprising an annular ring and extending from the inside of the ring, a plurality of spikes terminating in ends disposed generally to form an annular surface inside of the ring constructed to engage a stopper, the spikes being mounted on the ring so as to be similarly non-radially aligned, whereby the spikes positively grip the stopper only if the ring is rotated in the one direction, and slip off the stopper when the rotating means rotates in a direction opposite to the one direction.

Therefore, it is an advantageous feature of the invention that a stopper remover is provided that will slightly penetrate and positively grip a stopper, for retention, but only when rotated in one direction.

It is a related advantageous feature of the invention that such a stopper remover is provided that penetrates only the surface portion of the stopper, so as to be readily disengaged from the stopper by reversing the direction of rotation.

Another advantageous feature of the invention is the provision of a stopper remover that by virtue of its surface penetrability of the stopper, acts only on stopper materials and not inadvertently on the glass container surrounding such a stopper.

Other advantageous features will become apparent upon reference to the following description of the preferred embodiments, when read in light of the attached drawings.

DESCRIPTION OF THE PREFERRED EMBODIMENTS

The description hereinafter is directed to a stopper remover as is particularly useful in an analyzer that analyzes for analytes in patient samples such as blood, the preferred embodiment. In such an environment, it is particularly useful at the front end of such an analyzer, wherein test tube containers with positive patient identification are placed into the analyzer in a stoppered condition. In addition, the invention is useful for the removal of the stopper of any container, where such stopper can be penetrated at least at its surface by spikes, and regardless of the contents of the containers or subsequent processing of the contents.

As used herein, "spikes" refers to a plurality of generally straight and stiff members of a general cylindrical shape, having a length that is much greater than the diameter of the cylinder. Wires are particularly useful examples, discussed in greater detail hereinafter.

Figure 1:
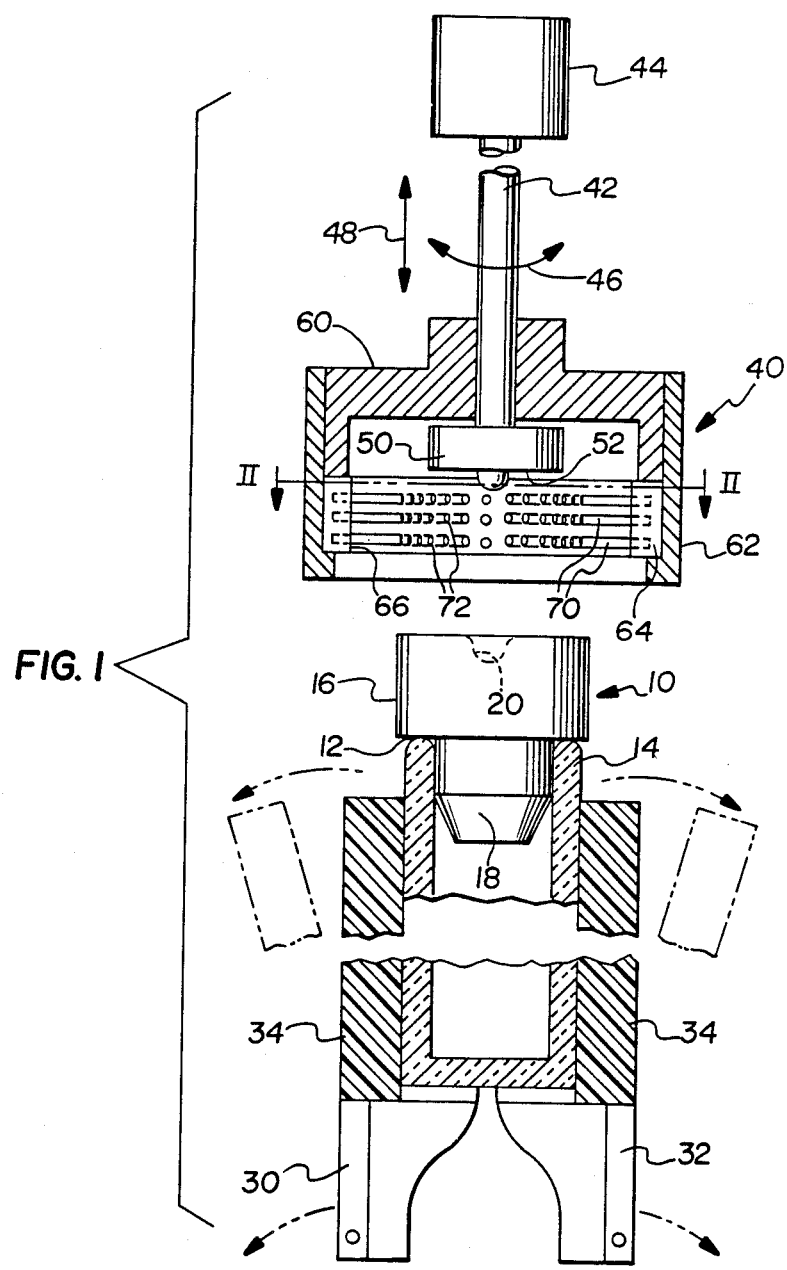
FIG. 1 is a fragmentary elevational view in section of a stopper remover constructed in accord with the invention.

Any stopper remover has to deal with two principal objects in the operation: the stopper, and the liquid container in which the stopper is inserted and held, usually by friction. In FIG. 1, stopper 10 is inserted into open end 12 of liquid container 14 that is basically a test tube. However, any kind of container can be used, provided it utilizes a stopper that can be gripped by the stopper remover of the invention. Although stopper 10 is shown as having an outer top portion 16, a narrower neck portion 18, and a central depression 20 in top portion 16, any shape is useful provided it can be properly gripped as discussed hereinafter.

To remove the stopper, relative motion must be provided to the stopper compared to the container. To that end, it is conventional to grip container 14 to hold it in place. Any conventional means is useful for this purpose, preferably means that releasibly engage container 14, such as opposable, pivotable jaws 30, 32, FIGS. 1 and 4, having elastomeric grippers 34 that contact and hold the container by friction, without however, so much force as to break the container (if made out of glass). (The released position of the jaws is shown in phantom, FIG. 1.)

Means 40 are the means that grip stopper 10, preferably along the outer surface thereof. Because means 40 are mounted on a drive shaft 42 connected to a conventional motor 44 that provides both rotary and linear motion (arrows 46 and 48, respectively), the gripped stopper is caused to move relative to container 14.

An optional feature provided in means 40 is a mating plunger 50 mounted on the end of shaft 42 opposite to the end connected to motor 44. Surface 52 of plunger 50 preferably is configured to match the contour of the top surface of stopper 10, including depression 20. Alternatively, however, plunger 50 can be omitted since the primary gripping and actuating member of means 40 is the inventive feature, next to be discussed.

Figure 2:
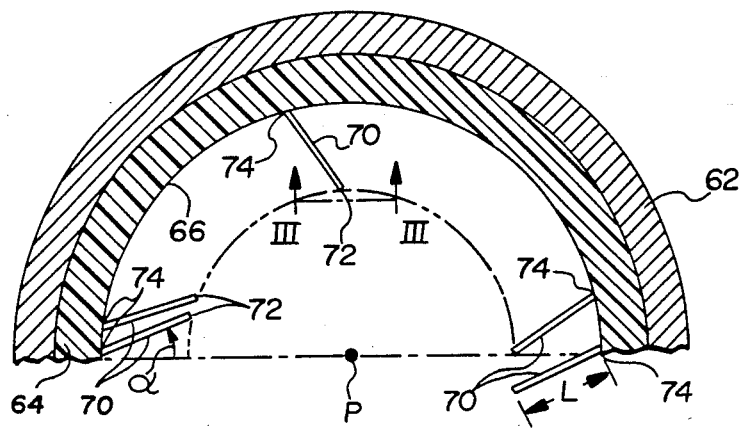
FIG. 2 is a fragmentary sectional view taken generally along the line II—II of FIG. 1.

In accord with one aspect of the invention, means 40 include a housing 60, having a general cup shape with an annular lip 62, and inside lip 62, an annular ring 64 having an inner surface 66. Emanating inwardly from surface 66 is a plurality of spikes 70 terminating in points at ends 72 that generally are disposed to create an annular surface that is generally parallel to and generally coincident with, surface 66 (FIGS. 1 and 2). The ends 74 of spikes 70 opposite to ends 72, FIG. 2, are embedded within ring 64, so as to each extend from surface 66 of ring 64 at a nonzero angle alpha, FIG. 2, to a diameter drawn through the center point P of ring 64. Angle alpha can be between about 30° and about 60°, and is preferably about 45°. Below 30°, there is too little differential between engaging in one rotational direction and not engaging in the other. Above 60°, the engagement during clockwise rotation also tends to start to decrease as the spikes become too tangentially aligned relative to the surface of the stopper. Angle alpha is preferably generally the same for each spike, and with the same sign (counterclockwise as shown), around the circumference of surface 66. It is because of the same sign of alpha, that the spikes are said to be "similarly non-radially aligned".

The purpose of such mounting of spikes 70 is to insure that, when upper portion 16 is inserted into the space between ends 72, with an outer diameter equal to or slightly larger than the diameter of the surface of ends 72, those ends penetrate slightly, that is, the surface only, of the stopper so as to engage the stopper, when ring 64 and its spikes are turned clockwise relative to point P (assumed to be stationary). However, if ring 64 is rotated the opposite direction (counterclockwise), ends 72 release from the surface of the stopper due to the wiping action induced by angle alpha, and spikes 70 release their grip on the stopper.

Figure 3:
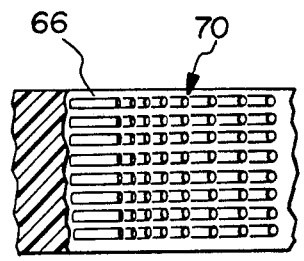
FIG. 3 is a partially diagrammatic elevational view taken generally along the line III—III of FIG. 2, to show a preferred packing density of the spikes.

A variety of packing densities is useful for the spikes, such packing density being depicted in FIG. 3. Preferably it is from 10 to about 25 spikes per cm² of curved surface, and most preferably about 15. These densities are selected because, below this lower value of about 10, the spikes tend to act more like individual nails and penetrate the surface of the stopper too much, possibly making release more difficult. The upper limit is not as significant, and is present only by way of economy since the additional cost of more spikes is not warranted.

As noted, wires are particularly useful examples, wherein length L, FIG. 2, is about 0.80 cm, and the diameter of the wire is about 0.025 cm. In addition, the lengths can be varied $\pm 0.1$ cm provided the diameter of the surface formed by ends 72 is adjusted to meet that provided by the O.D. of the stopper to be engaged.

Any material can be used for such spikes, so long as they are relatively stiff and yet flexible enough to allow some bending when rotated into engagement, and flexing back to straight when rotated out of engagement. To this end, metal wires having a relative stiffness of about 30,000 KSI, are particularly preferred.

Such construction of the spikes allows proper engagement of stoppers made of rubber, cork, or even plastic having a hardness below about Rockwell hardness L60 (as determined by American Standards measurement ASTM D785). It is a significant feature of these spikes that they will NOT engage the container 14, if the latter is made of glass or materials of similar hardness, as is customary. That is, spikes 70 are not capable of surface penetration of glass, nor will they significantly frictionally engage the same, even when ring 69 is rotated clockwise, FIG. 2. As a result, if means 40 is inadvertently applied too far down on a container so as to miss the stopper and grip the container itself, or if the stopper is missing, the spikes will not be able to grip the container sufficiently to apply significant torque thereto. This is in contrast to materials such as elastomers shaped with fingers aligned at angle alpha, which engage by friction alone. Such fingers will significantly frictionally engage glass as well as penetrable surfaces, thereby inducing enough torque against the container otherwise gripped in place as to possibly break the container.

Figure 4:
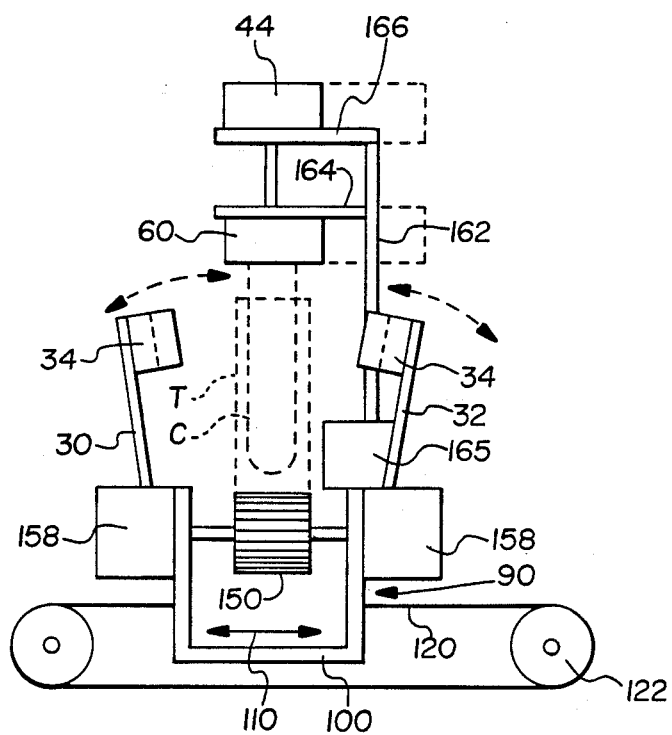
FIG. 4 is a fragmentary, partially schematic, elevational view illustrating the manner in which the stopper remover can be mounted in an analyzer.

Turning now to FIG. 4, the stopper remover comprising jaws 30, 32 and gripper means 40 can be mounted at any suitable location, and preferably a location 90 adjacent the loading end of an analyzer. As shown, it is mounted on a frame 100 that slides back and forth, arrow 110, on a rail (not shown), as induced by the translation back and forth of a belt 120 driven by pulley 122. Frame 100 in turn carries and endless conveyor belt 150, with jaws 30 and 32 being operated by motors 158 also mounted on frame 100. A vertically extending shaft 162 is connected to a rotating motor 165, and supports two platforms 164 and 166. Platform 164 can be used to support housing 60 in a bearing journal (not shown), while platform 166 supports motor 44. Motor 165 serves only to slightly rotate housing 60 and motor 44 out of the way of other parts, to a location shown in phantom, after a stopper has been removed.

Containers C, whether stoppered or unstoppered by the action of the stopper remover, preferably are carried by trays schematically shown as "T", FIG. 4, on belt 150. Jaws 30 and 32 and their gripping members 34 are constructed to slip through apertures (not shown) in the trays to contact containers C.

Frame 100 is rendered translatable, arrow 110, so that the frame and belt 150 can be aligned with alternate locations to take trays from more than one loading track. After the stopper is removed from any particular container, the liquid therein can be aspirated and then dispensed onto a test element, by other apparatus of the analyzer, not shown.

Coordination of the stopper remover with the other parts of the apparatus is handled automatically by conventional means, such as a microprocessor, not shown.

The invention has been described in detail with particular reference to preferred embodiments thereof, but it will be understood that variations and modifications can be effected within the spirit and scope of the invention.

What is claimed is:

1. In a stopper remover for automatically removing a stopper in a open end of an otherwise closed liquid container, the remover comprising first means for gripping said container against rotation, second means for gripping said stopper, and means for rotating said second means about an axis while said second means grips a stopper;

the improvement wherein said second gripping means includes engaging means for frictionally engaging a stopper while said rotating means rotates in only one direction, said engaging means comprising an annular ring and extending from the inside of said ring, a plurality of spikes terminating in ends disposed generally to form an annular surface inside of said ring constructed to engage a stopper, said spikes being mounted on said ring so as to be similarly non-radially aligned, whereby said spikes positively grip said stopper only if said ring is rotated in said one direction, and slip off the stopper when said rotating means rotates in a direction opposite to said one direction.

2. A stopper remover as defined in claim 1, wherein said spikes comprise wire bristles amounted on the inside surface of said ring so as to extend in said nonradial direction, the attachment of all of said bristles to said inside surface being at a nonzero angle to a diameter drawn across said ring at said attachment, that is generally the same and with the same sign for all of said bristles.

3. A stopper remover as defined in claim 2, wherein said angle is about 45°.

4. A stopper remover as defined in claim 1, 2 or 3, wherein said spikes are packed substantially together so that there are at least about 10 spikes per sq. cm. around said annular surface, whereby the end of each spike penetrates only a surface of said stopper and is readily disengaged from such stopper surface when said ring is rotated in said opposite direction.

* * * * *